United States Patent
Sutariya et al.

(10) Patent No.: US 11,173,152 B1
(45) Date of Patent: Nov. 16, 2021

(54) GLUTATHIONE-COATED NANOPARTICLES FOR DELIVERY OF MKT-077 ACROSS THE BLOOD-BRAIN BARRIER

(71) Applicant: UNIVERSITY OF SOUTH FLORIDA, Tampa, FL (US)

(72) Inventors: Vijaykumar Bhadabhai Sutariya, Tampa, FL (US); Umesh Kumar Jinwal, Temple Terrace, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/848,929

(22) Filed: Apr. 15, 2020

Related U.S. Application Data

(62) Division of application No. 16/271,018, filed on Feb. 8, 2019, now Pat. No. 10,758,520, which is a division of application No. 15/151,973, filed on May 11, 2016, now abandoned.

(60) Provisional application No. 62/164,291, filed on May 20, 2015.

(51) Int. Cl.
*A61K 31/4439* (2006.01)
*A61K 9/51* (2006.01)

(52) U.S. Cl.
CPC ............ *A61K 31/4439* (2013.01); *A61K 9/51* (2013.01); *A61K 9/5123* (2013.01); *A61K 9/5146* (2013.01); *A61K 9/5153* (2013.01)

(58) Field of Classification Search
CPC ...... A61K 9/5153; A61K 9/51; A61K 9/5146; A61K 9/5123; A61K 31/395; A61K 31/428; A61K 31/4439
See application file for complete search history.

(56) References Cited

U.S. PATENT DOCUMENTS

| 7,446,096 | B2 | 11/2008 | Wang et al. |
| 8,003,128 | B2 | 8/2011 | Kreuter et al. |
| 8,067,370 | B2 | 11/2011 | Trotter et al. |
| 8,067,380 | B2 | 11/2011 | Wang et al. |

(Continued)

FOREIGN PATENT DOCUMENTS

| WO | WO 2007/001448 | 1/2007 |
| WO | WO 2008/128123 | 10/2008 |
| WO | WO 2012/106713 | 8/2012 |

OTHER PUBLICATIONS

Koya et al. MKT-077, a Novel Rhodacyanine Dye in Clinical Trials, Exhibits Anticarcinoma Activity in Preclinical Studies Based on Selective Mitochondrial Accumulation. Cancer Research, 56, 538-543, Feb. 1, 1996.*

(Continued)

*Primary Examiner* — Lakshmi S Channavajjala
(74) *Attorney, Agent, or Firm* — Quarles & Brady LLP

(57) ABSTRACT

Nanoparticle based MKT formulation. MKT is encapsulated by poly(ethylene glycol)ylated (PEGylated) poly-(lactide-co-glycolide) (PLGA) to form nanoparticles (NPs). To induce trans-BBB permeability, glutathione (GSH) is coated on the resulting NPs. Newly generated MKT-NPs showed BBB permeability and tau reduction in experimental models. Specifically, brain-targeting MKT NPs were developed with a glutathione coating, characterized, and shown to permeate BBB permeation insert models as a therapeutic for Alzheimer's disease and related tauopathies.

6 Claims, 6 Drawing Sheets

(56) References Cited

U.S. PATENT DOCUMENTS

| | | | |
|---|---|---|---|
| 8,569,239 B2 | 10/2013 | Wang et al. | |
| 8,603,501 B2 | 12/2013 | Zale et al. | |
| 8,628,801 B2 | 1/2014 | Garreta et al. | |
| 9,808,448 B2 | 11/2017 | Gestwicki et al. | |
| 2005/0037075 A1 | 2/2005 | Farokhzad et al. | |
| 2007/0148074 A1 | 6/2007 | Sadoqi et al. | |
| 2011/0020457 A1 | 1/2011 | Panyam et al. | |
| 2018/0344657 A1 | 12/2018 | Halasz et al. | |

OTHER PUBLICATIONS

Chiba et al. MKT-077, localized lipophilic cation: antitumor activity against human tumor xenografts serially transplanted into nude mice. Anticancer Reserach 18(2A):1047-52, Mar.-Apr. 1998.*

Albanese et al., The Effect of Nanoparticle Size, Shape, and Surface Chemistry on Biological Systems. Annu Rev Biomed Eng. 2012. vol. 14: 1-16.

Kumar et al., Pegylated Dendritic Architecture for Development of a Prolonged Drug Delivery System for an Antitubercular Drug. Curr Drug Deliv. 2007. vol. 4: 11-19.

Lockman et al., Brain Uptake of Thiamine-Coated Nanoparticles. J Control Release. 2003. vol. 93: 271-282.

Geldenhuys et al., Brain-Targeted Delivery of Paclitaxel Using Glutathione-Coated Nanoparticles for Brain Cancers. J Drug Target. 2011. vol. 19 (No. 9): 837-845.

Kreuter. Nanoparticulate Systems for Brain Delivery of Drugs. Adv Drug Deliv Rev. 2001: vol. 47: 65-81.

Xie et al., Nanoparticulate Formulations for Paclitaxel Delivery across Mdck Cell Monolayer. The 13th Asia Pacific Confederation of Chemical Engineering Congress (APCChE). 2010: 1-2.

Olivier et al., Synthesis of Pegylated Immunoparticles. Pharmaceutical Research. 2002. vol. 19 (No. 8): 1137-1143.

Olivier et al., Indirect Evidence That Drug Brain Targeting Using Polysorbate 80-Coated Polybutylcyanoacrylate Nanoparticles Is Related to Toxicity. Pharmaceutical Research. 1999. vol. 16 (No. 12): 1836-1842.

Liu. Down-Regulation of Gamma-Glutamylcysteine Synthetase Regulatory Subunit Gene Expression in Rat Brain Tissue During Aging. Journal of Neuroscience Research. 2002. vol. 68: 344-351.

Parihar et al., Age-Related Decreases in Nad(P)H and Glutathione Cause Redox Declines before Atp Loss During Glutamate Treatment of Hippocampal Neurons. Journal of Neuroscience Research. 2008. vol. 86: 2339-2352.

Rebrin et al., Effects of Age and Caloric Intake on Glutathione Redox State in Different Brain Regions of C57bl/6 and Dba/2 Mice. Brain Research. 2007. vol. 1127: 10-18.

Robillard et al., Glutathione Restores the Mechanism of Synaptic Plasticity in Aged Mice to That of the Adult. PloS One. 2011. vol. 6 (No. 5): e20676.

Sasaki et al., Age-Related Changes of Glutathione Content, Glucose Transport and Metabolism, and Mitochondrial Electron Transfer Function in Mouse Brain. Nuclear Medicine and Biology. 2001. vol. 28: 25-31.

Geldenhuys et al., Brain-Targeted Delivery of Paclitaxel Using Glutathione-Coated Nanoparticles for Brain Cancers. Journal of drug targeting. 2011. vol. 19 (No. 9): 837-845.

Jinwal et al., Imbalance of Hsp70 Family Variants Fosters Tau Accumulation. The FASEB Journal. Apr. 2013. vol. 27: 1450-1459.

Park et al., Pegylated Plga Nanoparticles for the Improved Delivery of Doxorubicin. Nanomedicine: Nanotechnology, Biology, and Medicine. 2009. vol. 5: 410-418.

Jinwal et al., Chemical Manipulation of Hsp70 Atpase Activity Regulates Tau Stability. The Journal of Neuroscience. 2009. vol. 29 (No. 39): 12079-12088.

Garberg et al. In vitro Models for the Blood-Brain Barrier. Toxicol in Vitro. 2005. vol. 19. 299-334.

Wischke and Schedndeman. Principles of Encapsulating Hydrophobic Drugs in Pla/Plga Microparticles. Int J Pharm. 2008. vol. 364: 298-327.

Avgoustakis. Pegylated Poly(Lactide) and Poly(Lactide-Co-Glycolide) Nanoparticles: Preparation, Properties and Possible Applications in Drug Delivery. Current Drug Delivery. 2004. vol. 1(4): 321-33.

Bilati et al., Development of a nanoprecipitation method intended for the entrapment of hydrophilic drugs into nanoparticles. European Journal of Pharmaceutical Sciences, 2005. 24(1): p. 67-75.

Carroll et al., Brain-targeted delivery of Tempol-loaded nanoparticles for neurological disorders. Journal of Drug Testing, 2010. 18(9): p. 665-674.

Cecchelli et al., Modelling of the blood-brain barrier in drug discovery and development. Nature Reviews Drug Discovery, 2007. 6(8): p. 650-661.

Danhier et al., PLGA-based nanoparticles: an overview of biomedical applications. Journal of Controlled Release, 2012. 161(2): p. 505-522.

Etame et al., Design and Potential Application of PEGylated Gold Nanoparticles with Size-Dependent Permeation Through Brain Microvasculature, Nanomedicine: Nanotechnology, Biology, and Medicine, 2011, 7: p. 992-1000.

Friedhoff et al., Structure of tau protein and assembly into paired helical filaments. Biochimica et Biophysica Acta, 2000. 1502(1): p. 122-132.

Garberg et al., In Vitro Models for the Blood-Brain Barrier. Toxicol in Vitro, 2005. 19: p. 299-334.

Garcia et al., Endothelial cell-astrocyte interactions and TGFβ are required for induction of blood-neural barrier properties. Developmental Brain Research, 2004. 152(1): p. 25-38.

Garcia-Sierra et al., Conformational changes and truncation of tau protein during tangle evolution in Alzheimer's Disease. Journal of Alzheimer's Disease, 2003. 5(2): p. 65-77.

Geldenhuys et al., Brain-targeted delivery of paclitaxel using glutathione-coated nanoparticles for brain cancers. Journal of Drug Testing, 2011. 19(9): p. 837-845.

Geldenhuys et al., Brain-targeted delivery of doxorubicin using glutathione-coated nanoparticles for brain cancers. Pharmaceutical Development and Technology, 2015 (Epub Mar. 2014). 20(4): p. 497-506.

Ghaffarian and Muro, Models and Methods to Evaluate Transport of Drug Delivery Systems Across Cellular Barriers. J. Vis. Exp., 2013. (80):e50638.

Grover et al., Brain-Targeted Delivery of Docetaxel by Glutathione-Coated Nanoparticles for Brain Cancer. AAPS PharmSciTech, 2014. 15(6): p. 1562-1568.

Hatakeyama et al., Factors governing the in vivo tissue uptake of transferrin-coupled polyethylene glycol liposomes in vivo. International Journal of Pharmaceutics, 2004. 281(1): p. 25-33.

Hyman et al., Transcriptional and conformational changes of the tau molecule in Alzheimer's disease. Biochimica et Biophysica Acta, 2005. 1739(2): p. 150-157.

Jeganathan et al., The Natively Unfolded Character of Tau and Its Aggregation to Alzheimer-like Paired Helical Filaments. Biochemistry, 2008. 47(40): p. 10526-10539.

Jinwal et al., Hsc70 rapidly engages tau after microtubule destabilization. Journal of Biological Chemistry, 2010. 285(22): p. 16798-16805.

Jinwal et al., Preparation and characterization of methylene blue nanoparticles for Alzheimer's disease and other tauopathies. Curr Drug Deliv, 2014. 11(4): p. 541-550.

Kolarova et al., Structure and patholgy of tau protein in Alzheimer disease. International Jounral of Alzheimer's Disease, 2012. 2012:731526.

Koopaei et al., Docetaxel Loaded PEG-PLGA Nanoparticles: Optimized Drug Loading, In-vitro Cytotoxicity and In-vivo Antitumor Effect. Iranian Journal of Pharmceutical Researches, 2014. 13.3: p. 819-33.

Koren et al., Rhodacyanine derivative selectively targets cancer cells and overcomes tamoxifen resistance. Plos One, 2012. 7(4): p. e35566.

Lee et al. Glutathione PEGylated liposomal methylprednisolone (2B3-201) attenuates CNS inflammation and degeneration in murine oligodendrocyte glycoprotein induced experimental autoimmune encephalomyelitis. J Neuroimmunol, 2014. 274(1-2): p. 96-101.

(56) References Cited

OTHER PUBLICATIONS

Lockman et al., Brain uptake of thiamine-coated nanoparticles, Journal of Controlled Release, 2003. 93: p. 271-282.
Maccioni et al., The molecular bases of Alzheimer's disease and other neurodegenerative disorders. Archives of Meical Research, 2001. 32(5): p. 367-381.
Miyata et al., Synthesis and initial evaluation of YM-08, a blood-brain barrier permeable derivative of the heat shock protein 70 (Hsp70) inhibitor MKT, which reduces tau levels. ACS Chemical Neuroscience, 2013. 4(6): p. 930-939.
Propper et al., Phase I trial of the selective mitochondrial toxin MKT 077 in chemoresistant solid tumours. Annals of Oncology, 1999. 10(8): p. 923-927.
Sankar and Ravikumar. Biocompatability and Biodistribution of Suberoylanilide Hydroxamic Acid Loaded Poly (DL-lactide-co-glycolide) Nanoparticles for Targeted Drug Delivery in Cancer. Biomed Pharmacother., 2014. 68: p. 865-871.
Tatsuya et al., Pharmacokinetic analysis and antitumor efficacy of MKT, a novel antitumor agent. Cancer Chemotherapy and Pharmacology, 1999. 43(4): p. 295-301.
Thies and Bleiler, 2013 Alzheimer's disease facts and figures. Alzheimer's & Dementia: the Journal of the Alzheimer's Association, 2013. 9(2): p. 208-245.
Valdovinos-Flores and Gonsebatt, The role of amino acid transporters in GSH synthesis in the blood-brain barrier and central nervous system. Neurochemistry International, 2012. 61(3): p. 405-414.
Wacker, Nanocarriers for intravenous injection—The long hard road to the market. International Journal of Pharmaceutics, 2013. 457(1): p. 50-62.
Weisberg et al., In vivo administation of MKT causes partial yet reversible impairment of mitochondrial function. Cancer Research, 1996. 56(3): p. 551-555.
Wischke and Schwendeman, Principles of encapsulating hydrophobic drugs in PLA/PLGA microparticles. International Journal of Pharmaceutics, 2008. 364(2): p. 298-327.
Hatherell et al., Development of a three-dimensional, all-human in vitro model of the blood-brain barrier using mono-, co-, and tri-cultivation TRANSWELL models. Journal of Neuroscience Methods, 2011. 199(2): p. 223-229.
Jinwal et al. Preparation and Characterization of MKT-077 Nanoparticles for Treatment of Alzheimer's Disease and Other Tauopathies Pharmaceutical Nanotechnology, 2014. 2(4): p. 217.

\* cited by examiner

GLUTATHIONE-COATED NANOPARTICLES FOR DELIVERY OF MKT-077 ACROSS THE BLOOD-BRAIN BARRIER

CROSS-REFERENCE TO RELATED APPLICATIONS

The present application is a divisional of U.S. application Ser. No. 16/271,018, filed Feb. 8, 2019, which is the divisional of U.S. application Ser. No. 15/151,973, filed May 11, 2016, which claims the benefit of U.S. Provisional Application Ser. No. 62/164,291, filed May 20, 2015, each of which is hereby incorporated by reference herein in its entirety, including any figures, tables, nucleic acid sequences, amino acid sequences, or drawings.

BACKGROUND OF THE INVENTION

1. Field of the Invention

This invention relates, generally, to therapies for tauopathies and cancer. More specifically, it relates to delivery of MKT-077 nanoparticles across the blood-brain barrier for the treatment of such diseases and disorders.

2. Brief Description of the Prior Art

Alzheimer's disease (AD) is one of the most common causes of dementia and death in elderly populations. As average lifespan continues to increase, so does the prevalence of the disease. AD is characterized as cognitive impairment and disturbances that impact memory and behavior. AD is caused by neuronal inactivity and degeneration and leading to alterations in individuals' memory, thinking, speech, and behavior. Current estimates at the number of Americans currently suffering from AD place the figure at 5.2 million, incidence of which is sure to rise with the growth in the aging baby boomer generation, predicted to add an additional 10 million AD patients in the coming future. Currently, AD is the fifth most common cause of death in Americans over the age of 65 and the sixth most common leading cause of death in America [7]. It is imperative that new forms of therapies targeted to AD are developed to combat the morbidity of the disease. However, therapeutic intervention in AD is limited by the blood-brain barrier (BBB), which not only protects the brain by limiting the permeation of potential toxins into neural tissue but also by blocks certain drugs aimed at neurological disorders.

Tau, the aggregation of which indicates the presence of AD, belongs to the family of microtubule-associated proteins (MAP) and is an intrinsically disordered protein, lending it a number of potential cellular functionalities including regulation of vesicle transport and cell signaling [1-3]. Aggregation and conformational changes of tau protein render it unable to properly bind axonal microtubules in AD, leading to characteristic AD pathology [1, 4, 5]. Aberrant activity of tau leads to aggregation of tau protein into neurofibrillary bundles, causing toxicity and neurodegeneration in AD patients [6].

MKT-077 (MKT) is one such drug that has previously been shown to exhibit anti-tau and anti-cancer activities in cellular models. MKT is a highly water soluble cationic rhodacyanine dye [8, 9]. Biochemical analysis of MKT activity show that it selectively binds heat shock protein 70 (Hsp70) in cells, a mediator of tau protein activity that prevents its accumulation by promoting binding to tubulin microtubules [10, 11]. The interactions of MKT with Hsp70 make this drug an interesting target for cancer therapies based on its anti-cancer effects on melanoma and carcinoma of colon, breast, and pancreas [8].

However, phase 1 clinical trials of MKT in chemoresistant solid tumors revealed irreversible renal toxicity in rat, dog, and human subjects [9, 12].

Furthermore, despite MKT showing promise in reducing AD-related pathology in cellular models, it was shown that MKT has limited-to-no brain permeation due to blockage by the BBB [13]. The BBB is formed by the interaction of endothelial cells, astrocytes, and pericytes in neural tissue, create tight junctions that prevent toxins permeating into the brain by acting as a barrier. However, this same barrier inhibits drug delivery to alleviate AD's symptoms. For drugs to be effective against AD, it is essential that they are able to surmount the BBB, an obstacle to brain drug delivery that emerges from the interactions of endothelial cells with astrocytes and pericytes, which blocks the permeation of potential toxins into neural tissue [14]. As a result, a number of drug compounds are also unable to directly target the brain due to the BBB.

Attempts have been made to eliminate toxicity and traverse the BBB. For example, U.S. Pat. Nos. 8,067,370 and 8,569,239 to Wang et al. describes a biological delivery system comprising a carrier or an active compound, and a glutathione ligand or a glutathione derivative ligand. U.S. Pat. No. 8,003,128 to Kreuter et al. discusses a method of preparing a drug targeting system for administering a pharmacologically active substance to the CNS of a mammal across the BBB of the mammal using PLGA. U.S. Pat. No. 8,628,801 to Garreta teaches oral PEGylated nanoparticles for carrying biologically active molecules such as anti-tumor agents. U.S. Pat. No. 8,603,501 teaches pharmaceutical compositions including target-specific stealth nanoparticles useful in the treatment of cancer that includes the anti-cancer agent and a diblock copolymer of PEG and PLA or PLGA. U.S. Patent Application Publication No. 2007/0148074 to Sadoqi et al. describes polymer nanoparticles, for example including PLGA, to entrap fluorescent dyes and increase their stability in vitro and in vivo.

PCT Application Publication No. WO 2012/106713 to Basilion et al. teaches targeted nanoparticle conjugates including a polyethylene glycolylated nanoparticle, a hydrophobic therapeutic agent (e.g., anti-cancer agent) coupled to the surface of the nanoparticle, and a targeting moiety coupled to polyethylene glycol of the nanoparticle for targeting the composition to a cell associated with a disorder. PCT Application Publication No. WO 2008/128123 to Brader et al. discusses activated polymeric nanoparticle for targeted drug delivery, including a biocompatible polymer (e.g., PLGA), an amphiphilic stabilizing agent, an electrophile that selectively reacts with a targeting agent and places the targeting agent on a biodegradable nanoshell loaded on an active agent.

Koopaei, Mona N., Mohammad R. Khoshayand, Seyed H. Mostafavi, Mohsen Amini, Mohammad R. Khorramizadeh, Mahmood J. Tehrani, Fatemeh Atyabi, and Rassoul Dinarvand. "Docetaxel Loaded PEG-PLGA Nanoparticles: Optimized Drug Loading, In-vitro Cytotoxicity and In-vivo Antitumor Effect." *Iranian Journal of Pharmaceutical Researches* 13.3 (2014): 819-33. PubMed. Web. 6 Nov. 2014 describes docetaxel loaded PEG-PLGA nanoparticles as anticancer agents. Avgoustakis, Konstantinos. "Pegylated Poly(Lactide) and Poly(Lactide-Co-Glycolide) Nanoparticles: Preparation, Properties and Possible Applications in Drug Delivery." *Current Drug Delivery* 1.4 (2004): 321-33 teaches the preparation, properties and potential applications in drug delivery of PLGA-PEG nanoparticles. Sankar, Renu, and Vilwanathan Ravikumar. "Biocompatibility and Biodistribution of Suberoylanilide Hydroxamic Acid Loaded Poly (DL-lactide-co-glycolide) Nanoparticles for Targeted Drug Delivery in Cancer." Biomed Pharmacother. (2014), PubMed discusses suberoylanilide hydroxamic acid (SAHA) loaded poly (DL-lactide-co-glycolide) (PLGA) nanoparticles used to carry various chemotherapy agents into cancer cells for targeted drug delivery.

However, none of the foregoing references have been able to provide non-toxic nanoparticles and delivery system of MKT-077 that is also capable of successfully crossing the BBB. Accordingly, what is needed is a therapy and nanoparticle formulation that is capable of overcoming the foregoing toxicity and BBB permeability issues. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for brain-targeting therapies for tauopathies is now met by a new, useful, and nonobvious invention.

In an embodiment, the current invention is a composition itself or a method of treating a tauopathy or a cancer by administering a therapeutically effective amount of such composition. The composition comprises MKT admixed with a biocompatible, non-toxic polymer to form nanoparticles (e.g., average size of less than 300 nm) with MKT encapsulated therewithin. The nanoparticles each have a surface coated by glutathione (e.g., 2% w/v), such that the hydrophilic nature of glutathione allows MKT to effective permeate across the BBB despite the tight junctions of the BBB increasing their expression (during administration of the composition) to decrease toxicity that can cross the BBB.

The biocompatible, non-toxic polymer may include poly (ethylene glycol)ylated poly-(lactide-co-glycolide) or other suitable hydrophilic polymer to encapsulate the MKT, wherein this hydrophilicity facilitates an interaction of the glutathione with transporters present on the BBB.

MKT can have a sustained release from the nanoparticles of over about 72 hours, and during this time, about 100% of the MKT would be released from the nanoparticles.

The composition may further include a plurality of poly (ethylene glycol) end groups around the surface of each nanoparticle, where the end groups can be longer or otherwise extend further away from the nanoparticle surface than the glutathione that is disposed on the nanoparticle surface. This provides a surface area of the end grounds to interact with transporters present on the BBB.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
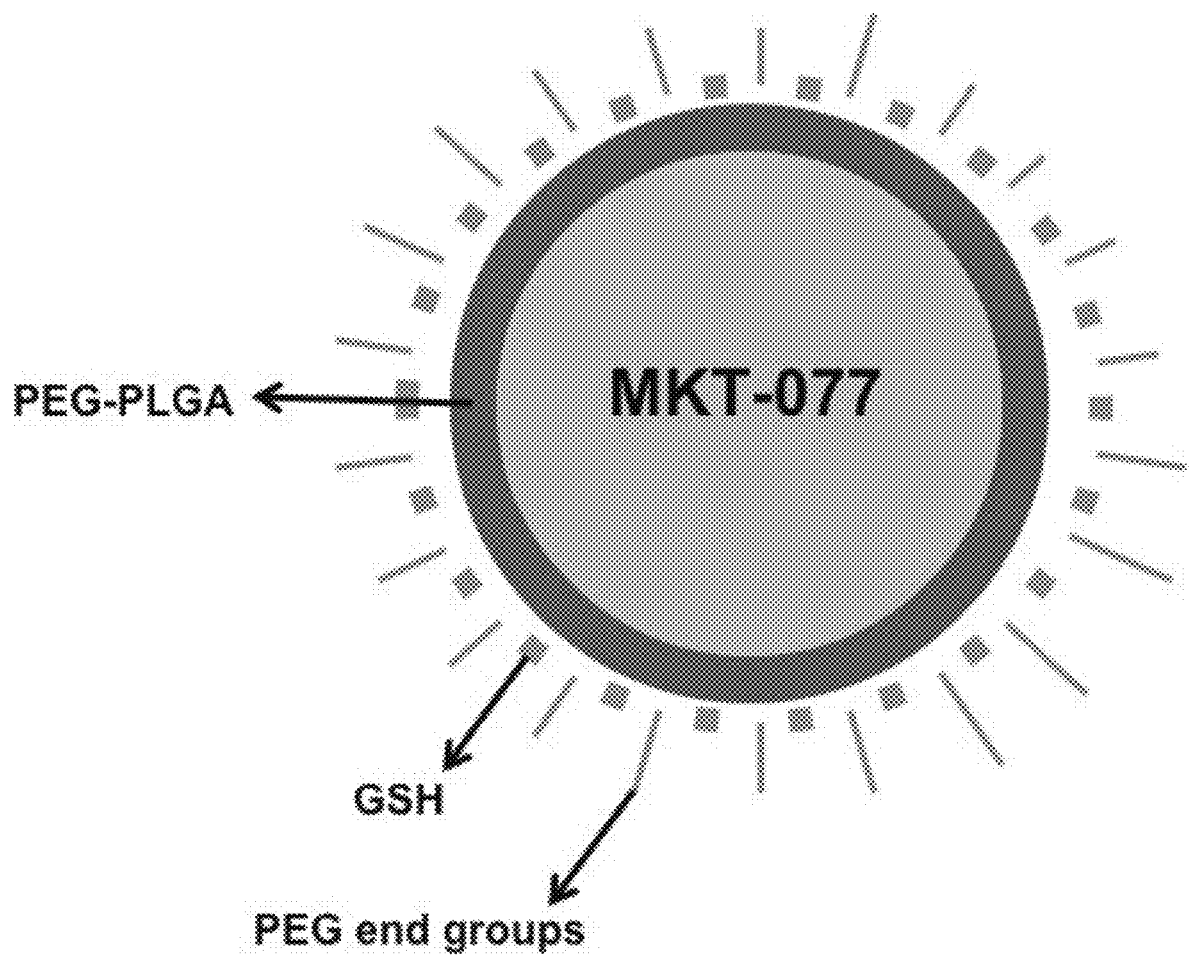
FIG. 1 is a schematic of formulated NPs. MKT drug is encapsulated in the hollow core of the NP sphere that is created as PEG-PLGA lipid chains coalesce upon evaporation of the oil phase during formulation. PEG end groups help the NPs evade the RES system and maintain hydrophilicity in blood. GSH is coated onto the NPs surface due to electrostatic interactions of charged functional groups on both GSH and PEG-PLGA vector. 178×142 mm (72×72 DPI)

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As discussed, MKT is a cationic rhodacyanine dye shown to interact with Hsp70 to regulate tau protein. MKT has shown anti-cancer effects on melanoma and carcinoma of colon, breast, and pancreas as well. However, phase 1 clinical trials of MKT in chemo-resistant solid tumors revealed irreversible renal toxicity in rat, dog, and human subjects. Furthermore, it was shown that MKT does not cross the BBB. As such, a nanoparticle based formulation was developed herein to overcome these particular toxicity and BBB permeability issues. In an embodiment, poly(ethylene glycol)ylated (PEGylated) PLGA nanoparticles (NPs) were used to encapsulate MKT, though other suitable encapsulation methods are contemplated herein as well. To induce trans-BBB permeability, glutathione (GSH) was coated on the resulting NPs, though other suitable hydrophilic molecules or formulations can be used as well for coating the NPs. Examples of alternatives to GSH include, but are not limited to, transport systems based on thiamine (or other amino acids) and transferrin for effective BBB permeation [33].

Though PEGylated PLGA is well known to be safe, biocompatible, non-toxic and restorable through natural pathways, other encapsulating polymers and formulations are contemplated herein as well for preparation of the NPs. Examples include, but are not limited to, lipids or oils, gelatin, sodium alginate, gum arabic, starch, tragacanth, shellac, paraffin wax, polylactic acid (PLA), polycaprolactone (PCL), methyl cellulose, pectin, carrageenan, alginates, methyl cellulose, casein, bovine albumin serum, chitosan, hydroxypropyl cellulose, hydroxypropyl methyl cellulose, ethyl cellulose, cellulose acetate phthalate, carmellose, polyvinyl alcohol, polystyrene, polyurethane, polyvinylpyrrolidone, polymethacrylate, polyvinyl acetate, polyhydroxyethyl methacrylate, polyvinyl chloride, polyacrylate, polyacrylamide, polyethylene glycol, polyester, polyurea, and polyamide, among other suitable polymers and formulations that may be used to prepare the NPs.

Examples of lipids that may be used include, but are not limited to, derivatives of glycerophospholipids, glycerolipids, sphingolipids, sterols, fatty acyl amides, prenols, ceramides, cholesterols, lecithin, glyceryl behenate (COMPRITOL), glyceryl palmitostearate (PRECIROL), glycerol monosterol (MONOSTEROL), glycerol disterate, sulfatides, phosphosphingolipids, phosphatidylcholines, phosphatidic acids, phosphatidylethanolamines, phosphatidylglycerols, phosphatidylserines, and phosphor lipids, among other suitable lipids that may be used to prepare multilayered nanostructures.

Examples of oils that may be used include, but are not limited to, safflower oil, sesame oil, corn oil, castor oil, coconut oil, almond oil, cotton seed oil, soybean oil, olive oil, mineral oil, spearmint oil, clove oil, lemon oil, peppermint oil, triacetin, tributyrin, ethyl butyrate, ethyl caprylateoleic acid, ethyl oleate, isopropyl myristate and ethyl caprylate, among other suitable oils that may be used to prepare multilayered nanostructures.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. Administration can be accomplished in number of ways including, but not limited to, parenteral (such term referring to intravenous and intra-arterial as well as other appropriate parenteral routes), subcutaneous, peritoneal, inhalation, vaginal, rectal, nasal, or instillation into body compartments.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art, unless otherwise noted.

Administration will often depend upon the amount of compound administered, the number of doses, and duration of treatment. In an embodiment, multiple doses of the agent are administered. The frequency of administration of the agent can vary depending on any of a variety of factors, such as extent of tau protein levels, tumor volume, and the like. The duration of administration of the agent, e.g., the period of time over which the agent is administered, can vary, depending on any of a variety of factors, including patient response, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

As used herein, the term "composition" is intended to encompass a product comprising the specified ingredients, in the specified amounts, as well as any product which results, directly or indirectly, from combination of the specified ingredients in the specified amounts. Generally, the specified ingredients, or pharmaceutically acceptable salts and derivatives thereof, are suitable agents for use in the diagnosis, mitigation, treatment, cure, or prevention of disease in a subject, specifically but not exclusively effective in the treatment and/or prevention of estrogen receptor-mediated disorders, including specifically the treatment and/or prevention of breast cancer, when administered in an effective amount to a subject in need thereof.

As used herein, the terms "nanostructure" and "nanoparticle" may be used interchangeably to refer to any polymeric micelle, lipid micelle, hybrid lipid-polymer micelle, liposome, niosomes, transferosome, liponanoparticle, lipid nanoparticles, nanostructured lipid nanocarriers (NLC), solid lipid nanoparticles (SLN), hybrid lipid-polymer nanostructures, bicelle, polymerosomes, lamellar structures, and lipid vesicles, among other delivery systems that can be used suitably to deliver one or more active pharmaceutical agent(s).

A combination of polymers and/or lipids can be used to prepare the nanoparticles. The nanoparticles can be prepared using electrostatic interaction, self-assembly, ionotropic gelation, cross-linking, coacervation, homogenization-solvent evaporation, sonication, ultrasound, nanoprecipitation, spray drying, high pressure homogenization, layer by layer, freeze drying, hot-melt homogenization, film formation, co-solvent evaporation, high pressure instruments such as NANODEBEE, and coating or solvent emulsion methods, alone or in combination.

As used herein, the term "neoproliferative disease" means a neoplasm, cancer, or precancerous lesion. The neoplasm or cancer may be benign or malignant.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The pharmaceutical compositions of the subject invention can be formulated according to known methods for preparing pharmaceutically useful compositions. Furthermore, as used herein, a "pharmaceutically acceptable excipient," "pharmaceutically acceptable diluent," "pharmaceutically acceptable carrier," or "pharmaceutically acceptable adjuvant" means any of the standard pharmaceutically acceptable carriers, such as a solvent, suspending agent or vehicle, for delivering the compound or compounds in question to the mammal. The carrier may be liquid or solid and is selected with the planned manner of administration in mind. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, liposomes, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. The carrier can also include any and all other vehicles, coatings, diluents, antibacterial and antifungal agents, isotonic and absorption delaying agents, buffers, carrier solutions, suspensions, colloids, and the like. Formulations are described in a number of sources that are well known and readily available to those skilled in the art. Except insofar as any conventional media or agent is incompatible with the active ingredient, its use in the therapeutic compositions is contemplated. For example, Remington's Pharmaceutical Sciences (Martin E W [1995] Easton Pa., Mack Publishing Company, $19^{th}$ ed.) describes formulations which can be used in connection with the subject invention. "A pharmaceutically acceptable excipient, diluent, carrier and/or adjuvant" as used in the specification and claims includes one or more such excipients, diluents, carriers, and adjuvants.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

As used herein, the term "precancerous" refers to cells or tissues that have characteristics relating to changes that may lead to malignancy or cancer, such as mutations controlling cell growth and proliferation. Examples include adenomatous growths in breast and prostate tissue, or for example, conditions of dysplastic nevus syndromes, polyposis syndromes, prostatic dysplasia, and other neoplasms, whether clinically identifiable or not.

The term "prevention" is used herein to refer to the management of the factors that could lead to disease or disorder, so as to prevent the occurrence of the disease or disorder. Specifically, the disease or disorder includes, but is not limited to, various tauopathies and cancers.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "safe and effective amount" refers to the quantity of a component or composition that is sufficient to yield a desired therapeutic response without undue adverse side effects (such as toxicity, irritation, or allergic response) commensurate with a reasonable benefit/risk ratio when used in the manner of this invention for the treatment and/or prevention of tauopathies and cancer.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to tauopathies, an effective amount comprises an amount sufficient to cause a reduction in tau protein levels or a reduction in growth of tau protein levels. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation.

In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, "treat", "treatment", "treating", and the like refer to acting upon a condition (e.g., tau protein aggregation) with an agent (e.g., MKT-077) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reducing tau protein levels, increasing cognitive abilities). As it pertains to cancer treatment, beneficial or desired clinical results include, but are not limited to, any one or more of the following: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, remission (whether partial or total).

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

Study

The current study evaluates the formulation and characterization of MKT encapsulated by a brain-targeted vector, such as PEG-PLGA NPs via nanoprecipitation, coated in a sufficient amount (e.g., 2% w/v) of GSH to obtain greater BBB permeation and decrease toxicity in the target area or drug delivery (i.e., brain). PLGA NPs are FDA approved and widely used in drug delivery due to their biodegradability into the biocompatible compounds, lactic and glycolic acid, endocytosis through clathrin-mediated pathways, and low toxicity [15]. PEG conjugation to the PLGA polymer increases bioavailability of the NPs in blood due to greater solubility and low uptake by the reticuloendothelial system (RES) [16].

This formulation is contemplated to be a non-toxic alternative to reduce pathological tau protein aggregation associated with AD and other tauopathies. Average nanoparticle size was found to be about 275.73±12.41 nm, suitable for intravenous administration and brain permeation, and have polydispersity index of about 0.066±0.051. The encapsulation efficiency of the MKT NPs was about 25%. The nanoparticles showed steady, sustained release of MKT in in vitro settings. TRANSWELL in vitro BBB model permeation studies showed the permeation of nanoparticles across the TRANSWELL model to be greater than drug solution over 48 hours. As such, the formulation developed and described herein has shown promise and potential efficacy as a potential therapy against AD and other tauopathies. The targeting system for MKT could be an effective sustained release treatment for AD and other related neurological disorders.

GSH was used to coat the NPs to induce trans-BBB permeability. GSH is synthesized in cells from amino acid precursors and acts in reducing oxidative stress to neural tissue. In addition, GSH transporters are abundantly found at the BBB interface and assist in the transport of various compounds across the BBB [17]. A number of GSH-coated NP delivery systems have been reported by the current inventors for the brain-targeted delivery of the AD drug, Methylene blue [18], the Parkinson's drug, tempol [19], and various cancer drugs such as paclitaxel [20], doxorubicin [21], docetaxel [14], and methyl prednisolone [22]. Furthermore, in vivo studies of 6-coumarin loaded GSH PLGA NPs injected peritoneally in C57BL/6 mice revealed higher concentration of 6-coumarin in brain tissue as opposed to 6-coumarin uncoated PLGA NPs [20].

To study trans-BBB permeation of MKT NPs, in particular, however, the present study utilizes TRANSWELL permeable inserts for establishing an in vitro BBB model. TRANSWELL permeable inserts allow for the seeding of multiple cell lines on the apical and basolateral sides of the insert and sharing of media, thereby being considered the "gold standard" for trans-membrane studies [23]. The model was established using rat brain endothelial (RBE4) and rat astrocytic (C6) cells; the interactions of astrocytes with endothelial cells promotes the expression of BBB-specific tight junctions and transport proteins in endothelial cells [14, 24].

The present study formulates and characterizes MKT NPs and also demonstrates brain-targeted delivery of MKT NPs as a potential treatment against AD and other tauopathies. Cellular studies in AD models show that the GSH-coated MKT NPs (MKT Glu-NPs) are effective in reducing tau protein levels. TRANSWELL in vitro BBB permeation studies show that MKT Glu-NPs were also able to cross the BBB better than MKT drug solution alone.

These newly generated MKT-NPs showed BBB permeability and tau reduction in experimental models. This embodiment of the formulation can be seen in FIG. 1. Although it can be seen in this embodiment that the PEG end groups may be longer than GSH, which could shield the interaction between the GSH and its transporters, the PEG group does not cover entire surface area of nanoparticles. There is sufficient surface area available for interaction with the BBB transporters. Moreover, PEG is very hydrophilic which will help the interaction of hydrophilic GSH with transporters present on the BBB. Higher BBB permeation has been shown by GSU coating on liposome with PEG end group [22]. The NPs show promise as a potential therapeutic option against AD and other tauopathies.

Materials and Methods
Materials

PEG-PLGA (5050 DLG, mPEG 5000) was synthesized and purchased from LAKESHORE BIOMATERIALS (Birmingham, Ala.). MKT was purchased from SIGMA-ALDRICH (St. Louis, Mo.). Reduced GSH was purchased from FISHER BIOREAGENTS (THERMO FISHER SCIENTIFIC Inc., Pittsburgh, Pa.). Phosphate buffered saline (PBS) was purchased from CELLGRO (CORNING Inc., Corning, N.Y.). Acetone and methanol were both purchased from SIGMA ALDRICH (St. Louis, Mo.).

Preparation of GSH-Coated PEG-PLGA NPs

NPs encapsulating MKT were formulated by known methodologies, such as the nanoprecipitation method according to a protocol previously reported by the current inventors [18]. Briefly, 3.5 mg of MKT was dissolved in 100 µL of methanol and added dropwise to 4 mL of acetone. 120 mg of PEG-PLGA was subsequently added to the acetone and the solution was vortexed for the proper dissolution of all components. The resulting solution was added dropwise to 8 mL of deionized $H_2O$ (stirring at 300 rpm). The acetone was allowed to completely evaporate overnight. The resulting NP solution was centrifuged at 4500×g for 35 minutes to collect the NPs. The resulting supernatant was decanted to discard any unencapsulated drug and free polymer and replaced with 10 mL of fresh deionized $H_2O$. GSH was coated onto the NPs according to a method previously reported by the current inventors [20]. 20 mg of GSH was added to 1 mL of the NPs solution to achieve a 2% w/v GSH coating and was allowed to incubate at room temperature for 30 minutes prior to use.

Characterization of NPs Formulations

The blank NPs, MKT NPs, and MKT Glu-NPs were characterized for physical parameters. Particle size and polydispersity index (PDI) were analyzed through dynamic light scattering (DLS) using the DYNAMIPRO PLATE READER (WYATT TECHNOLOGY, CA). Samples were diluted to fit instrumental specifications.

Scanning Electron Microscopy (SEM) Analysis of NPs Formulations

SEM was utilized to investigate the physical integrity of blank NPs, MKT NPs, and MKT Glu-NPs. JOEL JSM-6490LV (JOEL INDUSTRIES, Tokyo, Japan) was used to visualize the samples. The samples were diluted according to instrumental specifications and were loaded onto aluminum cylinders coated with an adhesive carbon polymer. NPs formulations were viewed in 65,000× magnification. 4 kV acceleration voltage was used to visualize the blank NPs and MKT NPs formulations and 8 kV acceleration voltage was used to visualize the MKT Glu-NPs.

Determination of Entrapment Efficiency

The methanol method was employed to determine the entrapment efficiency of MKT by the NPs [20]. 1 mL of MKT NPs was ultracentrifuged for 5 minutes at 12,000 rpm to separate the NPs from solution. The resulting supernatant was carefully removed and replaced with 1 mL of cold methanol and placed in 4° C. refrigerator overnight to allow for a complete extraction of MKT from the NPs. The methanol supernatant was read by UV spectroscopy (COLE PARMER, Vernon Hills, Ill.) at a wavelength of 492 nm ($\lambda_{max}$) and compared to standard dilutions of MKT drug in methanol ($r^2$=0.9934). The entrapment efficiency was calculated by using the following formula:

$$\text{entrapment efficiency} = \frac{\text{actual drug yield}}{\text{theoretical drug yield}} \times 100\%$$

In Vitro Drug Release

The drug release profile of MKT from MKT NPs and MKT Glu-NPs was investigated using a method previously described by the current inventors in [14]. 0.05 mg equivalent of MKT aqueous solution, MKT NPs, and MKT Glu-NPs were placed in dialysis membrane tubing (MWCO 10,000 kDa) and placed in 20 mL of release medium comprised of PBS (pH 7.4) stirring at 100 rpm and 37° C. 1 mL aliquots were removed at predetermined intervals over 7 days and analyzed by UV spectroscopy at wavelength of 492 nm ($\lambda_{max}$) and compared to UV absorbance of standard aqueous dilutions of MKT drug ($r^2$=0.9943).

Cell Culture

BBB model: C6 (rat astrocytoma) cells were purchased from ATCC (CCL-107), and RBE4 (rat brain endothelial) cells were obtained via gift. Cell culture plates and flasks were purchased from CORNING Inc. (Corning, N.Y.). TRANSWELL permeable inserts were purchased from CORNING Inc. (No. 3460; Corning, N.Y.). Ham's F10 and MEM media and PBS solution were purchased from CELLGRO (CORNING Inc., Corning, N.Y.). 1% penicillin and streptomycin solution and fetal bovine serum (FBS) were purchased from INVITROGEN (THERMO FISHER SCIENTIFIC Inc., Pittsburgh, Pa.). Rat tail collagen I and human recombinant diluted basic fibroblast growth factor were purchased from BD BIOSCIENCES (San Jose, Calif.).

Cell Culture, Treatment and Immunoblotting

AD model: HeLa cells stably expressing human tau were maintained in OPTIMEM media as described earlier [18]. Treatment with nanoparticles or control were performed for 24 hours and samples analyzed by western blotting, as described earlier [18].

Trans-Endothelial Electrical Resistance (TEER) of TRANSWELL BBB Model

The TEER of the BBB model was studied to investigate the expression of BBB-specific tight junctions in the TRAN- SWELL model according to a method previously reported by the current inventors [14]. TEER values were measured at the beginning and end of the BBB permeation study. Media was aspirated from the inserts and replaced with PBS before taking TEER measurements. STX2 electrode and EVOM$^2$ epithelial voltohmmeter (WORLD PRECISION Instruments, Sarasota, Fla.) were used to measure TEER.

It has been shown that TEER values can be used investigate in vitro the expression of BBB-specific tight junctions ([18], [21], [29]-[31]).

In Vitro BBB Permeation Model

A TRANSWELL in vitro BBB model was established to study the BBB permeation of MKT NPs and MKT Glu-NPs compared to drug solution according to a method previously described by the current inventors in [18]. TRANSWELL permeable inserts were treated with 0.1% rat tail collagen I on the apical and basolateral sides. After 24 hours, C6 (rat astrocytoma) cells were seeded onto the basolateral side of the permeable insert ($5 \times 10^4$ cells). After 48 hours, RBE4 (rat brain endothelial) cells were seeded onto the apical side of the permeable ($5 \times 10^4$ cells). Cells were bathed in 1:1 mixture of Ham's F10:MEM media supplemented with 10% FBS with 1.5 mL in the basolateral chamber and 0.5 mL in the apical chamber, and were allowed to incubate (37° C. and 5% $CO_2$) for 24 hours until confluence was established.

After 24 hours, media was replaced with a 1:1 mixture of Ham's F10:MEM media supplemented with 1% FBS (experimental media), and cells were treated with 10 μM equivalent treatments of MKT aqueous drug solution, MKT NPs, and MKT Glu-NPs. 1 mL media samples were aliquoted from the basolateral chamber at predetermined intervals over a 48-hour period to investigate the trans-BBB permeation of the treatments. Aliquots were read by UV spectroscopy (at wavelength of 492 nm ($\lambda_{max}$) and compared to UV absorbance of standard dilutions of MKT drug in experimental media ($r^2$=0.9990).

Results

Characterization of NPs Formulations

Three different samples of NPs formulations were characterized for physically-relevant parameters. Size and PDI were investigated through DLS; data is presented in Table 1. Blanks NPs were found to have size of 244.37±14.45 nm and PDI of 0.0498±0.395; MKT NPs were found to have size of 275.73±12.41 nm and PDI of 0.0657±0.0508; and MKT Glu-NPs were found to have size of 230.17±8.02 nm and PDI of 0.0302±0.0152. Samples were read in triplicate (n=3) and reported as mean values ±SD. The MKT NPs were significantly larger than blank NPs (p≤0.05).

TABLE 1

Data from physical characterization of NPs formulations via DLS. Samples were read in triplicate (n = 3) and reported as mean value ± SD.

| | Size (nm) | PDI |
|---|---|---|
| Blank NPs | 244.37 ± 14.45 | .0498 ± .0395 |
| MKT NPS | 275.73 ± 12.41 | .0657 ± .0508 |
| MKT Glu-NPs | 230.17 ± 8.02 | .0302 ± .0152 |

Scanning Electron Microscopy (SEM) Analysis of NPs Formulations

Figure 2:
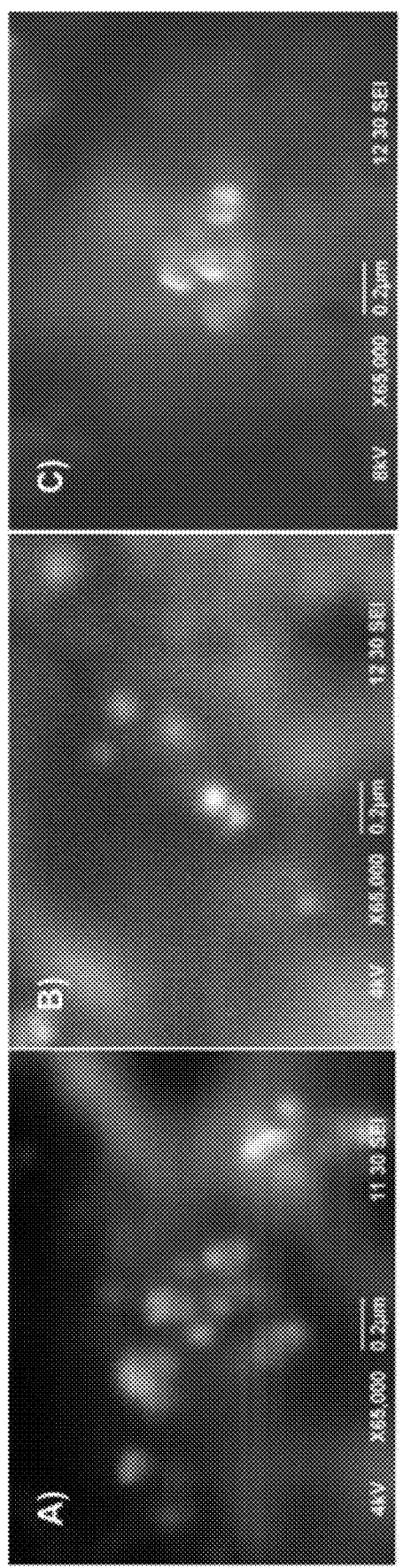
FIG. 2A is an SEM visualization of blank NPs. Samples were diluted according to instrument specifications and visualization was done through JOEL JSM-6490LV (JOEL Industries, Tokyo, Japan). Samples were read at 65,000× magnification and 4 kV acceleration voltage for blank NPs and MKT NPs and 8 kV acceleration voltage for MKT Glu-NPs samples. 267×67 mm (72×72 DPI)
FIG. 2B is an SEM visualization of MKT NPs. Samples were diluted according to instrument specifications and visualization was done through JOEL JSM-6490LV (JOEL Industries, Tokyo, Japan). Samples were read at 65,000× magnification and 4 kV acceleration voltage for blank NPs and MKT NPs and 8 kV acceleration voltage for MKT Glu-NPs samples. 267×67 mm (72×72 DPI)
FIG. 2C is an SEM visualization of MKT Glu-NPs. Reflective coating on surface of MKT Glu-NPs suggests the successful coating of GSH onto the NPs formulation. Samples were diluted according to instrument specifications and visualization was done through JOEL JSM-6490LV (JOEL Industries, Tokyo, Japan). Samples were read at 65,000× magnification and 4 kV acceleration voltage for blank NPs and MKT NPs and 8 kV acceleration voltage for MKT Glu-NPs samples. 267×67 mm (72×72 DPI)

JOEL JSM-6490LV (JOEL Industries, Tokyo, Japan) SEM was used to visualize the morphology of blank NPs (FIG. 2A), MKT NPs (FIG. 2B), and MKT Glu-NPs formulations (FIG. 2C). Surface analysis of NP formulations showed that physical integrity was maintained by all samples. Size and size distribution of respective NP formulations visualized through SEM corroborated with data obtained via DLS.

Determination of Entrapment Efficiency

The efficiency of MKT encapsulation by the MKT NPs formulation was investigated through the methanol method. UV spectroscopy analysis revealed the encapsulation efficiency to be 29.98±1.37%. The values yielded by the encapsulation efficiency study were used to determine the molarity of the NPs solution and select the proper volume of NP formulations utilized in cell treatments. Data was obtained in triplicate (n=3) and reported as mean encapsulation efficiency ±SD.

In Vitro Drug Release

Figure 3:
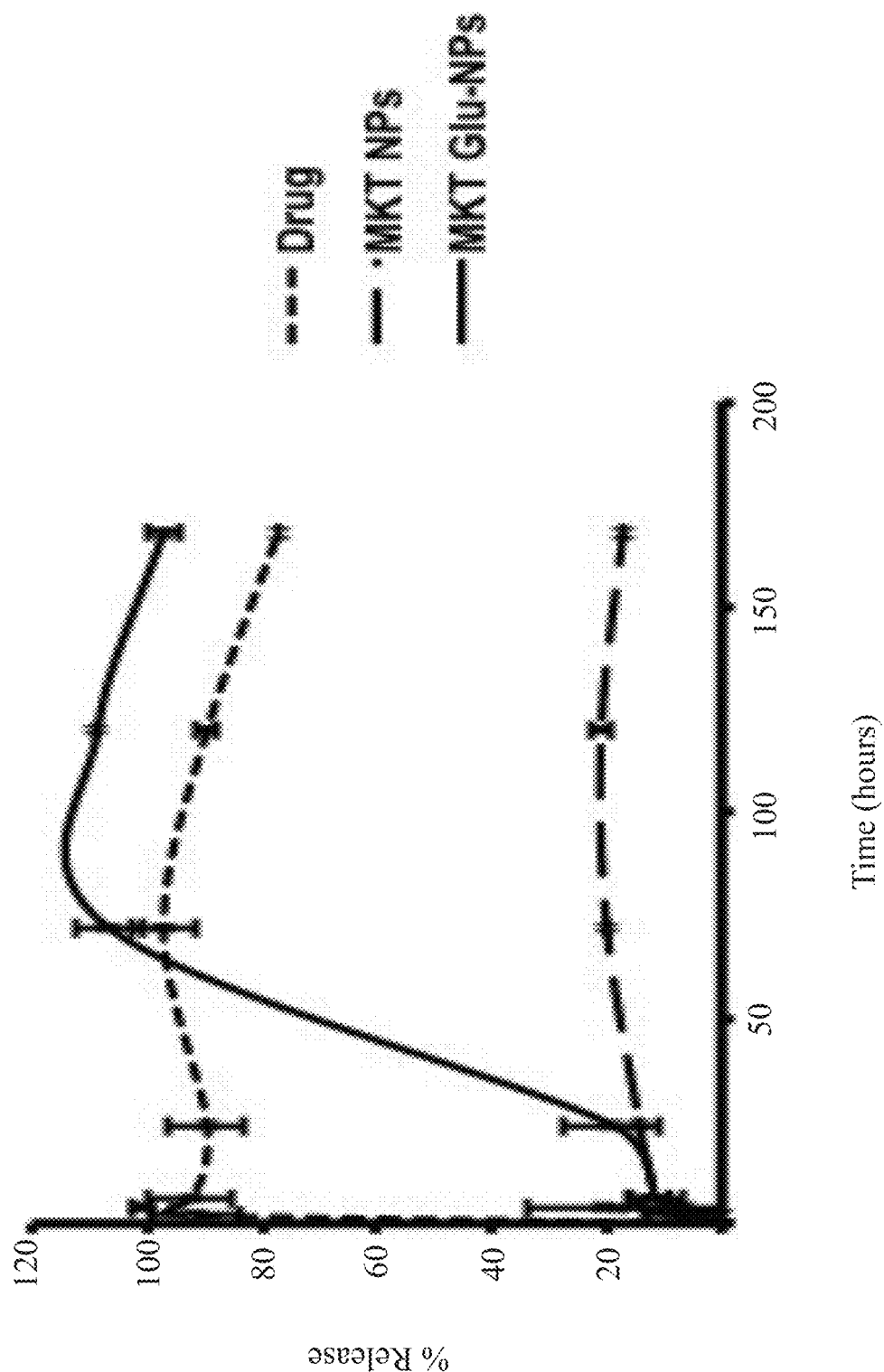
FIG. 3 is a graphical illustration showing in vitro drug release data of drug solution, MKT NPs, and MKT Glu-NPs over a 7-day study period. MKT Glu-NPs exhibited sustained drug release up to 72 hours until full content of drug was released from NP vector, and MKT NPs showed sustained drug release up to 7 days. Samples were read through UV spectroscopy at wavelength of 492 nm ($\lambda_{max}$) in triplicate (n=3) and reported as mean percentage drug release ±SD. 242×74 mm (72×72 DPI)

In vitro release studies were carried out to investigate the rate of drug release by the NP formulations. Three (3) samples were studied—aqueous MKT solution, MKT NPs, and MKT Glu-NPs—over 7 days. Approximately 100% of the drug was released by the aqueous solution within the initial 4 hours of the study; approximately 100% of the drug was released by the MKT Glu-NPs in 72 hours (FIG. 3); and approximately 25% of the drug was released from the MKT uncoated NPs at the end of the 7-day study (FIG. 3). The aqueous drug solution showed a rapid release of the drug, and both NP formulations investigated showed a sustained release of the drug from the NP polymer due to slower degradation of the polymer matrix of NPs. All samples showed initial burst release of the drug. Samples were read in triplicate (n=3) and reported as mean percent drug release ±SD.

Trans-Endothelial Electrical Resistance (TEER) of TRANSWELL BBB Model

TEER values of the TRANSWELL in vitro BBB model are presented in Table 2. TEER values were read for inserts of all treatment groups (i.e., drug solution, MKT NPs, MKT Glu-NPs) before treatment at 0 hours and after treatment course was completed at 48 hours. TEER values were significantly higher after treatment for all experimental groups than before treatment (p≤0.05). TEER values were read in quadruplicates (n=4) and reported as mean resistance (Ω cm$^2$) ±SD.

TABLE 2

TEER values for all treatment groups taken before and after treatment. TEER values were measured with STX2 electrode and EVOM$^2$ epithelial voltohmmeter (WORLD PRECISION Instruments, Sarasota, FL) and read in quadruplicates (n = 4) reported as mean Ωcm$^2$ ± SD.

| | Before treatment (Ωcm$^2$) | After treatment (Ωcm$^2$) |
|---|---|---|
| Drug solution | 251.44 ± 17.48 | 294.56 ± 18.15 |
| MKT NPs | 301.84 ± 54.52 | 386.70 ± 80.23 |
| MKT Glu-NPs | 271.41 ± 14.18 | 354.29 ± 24.44 |

In Vitro BBB Permeation Model

Figure 4A:
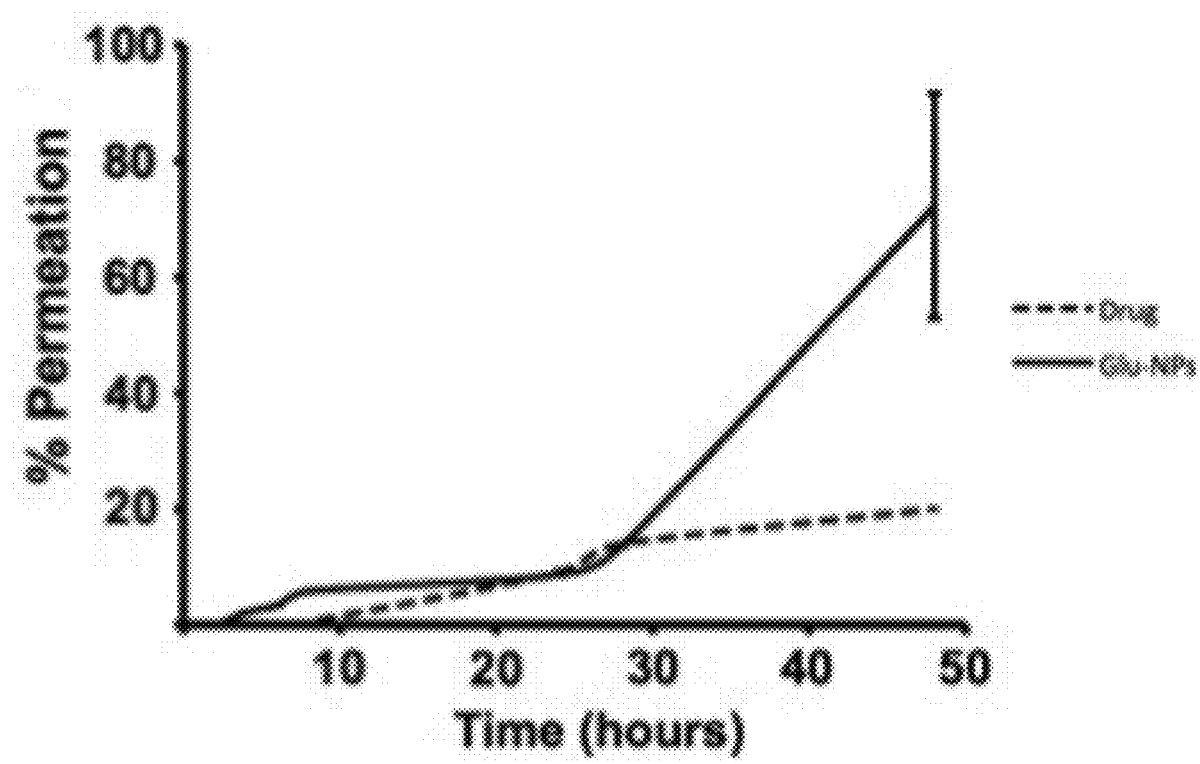
FIG. 4A is a graphical illustration showing trans-BBB brain permeation of drug solution vs. MKT Glu-NPs, obtained through TRANSWELL in vitro BBB model established through the co-culture of RBE4 (rat brain endothelial) cells with C6 (rat astrocytoma) cells. MKT Glu-NPs showed the greatest permeation through the BBB model over the 48-hour study period. Treatments were carried out in quadruplicate (n=4) and read through UV spectroscopy at 492 nm ($\lambda_{max}$) for drug content. Values are reported as mean percent drug permeated ±SD. 238×75 mm (72×72 DPI)
Figure 4B:
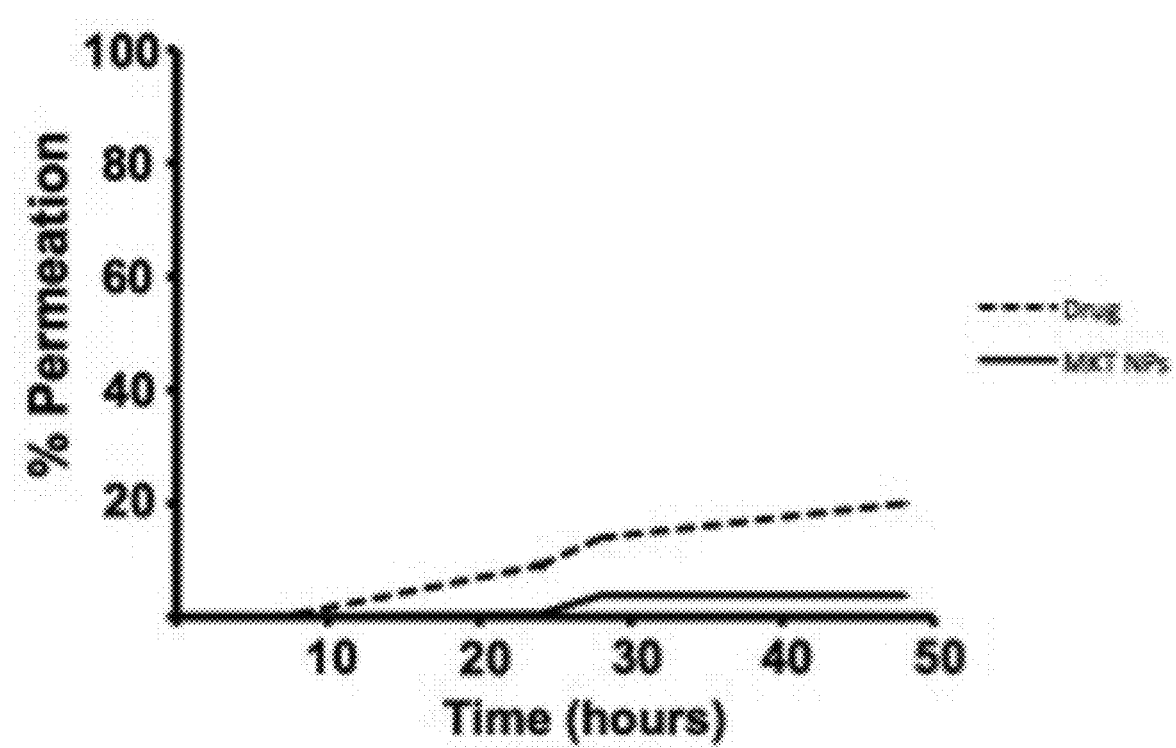
FIG. 4B is a graphical illustration showing trans-BBB brain permeation of drug solution vs. MKT NPs, obtained through TRANSWELL in vitro BBB model established through the co-culture of RBE4 (rat brain endothelial) cells with C6 (rat astrocytoma) cells. MKT Glu-NPs showed the greatest permeation through the BBB model over the 48-hour study period. Treatments were carried out in quadruplicate (n=4) and read through UV spectroscopy at 492 nm ($\lambda_{max}$) for drug content. Values are reported as mean percent drug permeated ±SD. 238×75 mm (72×72 DPI)

TRANSWELL permeable inserts were used to establish an in vitro BBB model to investigate the trans-BBB permeability potential of equivalent concentrations of NP formulations as compared to aqueous drug solution over a 48-hour study period. At the end of the 48-hour study period, 20% of the drug solution permeated, 3% of the MKT NPs permeated through (FIG. 4A), and 72% of the MKT Glu-NPs permeated through the BBB model (FIG. 4B). The permeation profiles of the drug solution and MKT Glu-NPs were relatively similar for the first 24 hours of the study. MKT Glu-NPs drastically increased trans-BBB permeation between 24-48 hours while permeation of drug solution was relatively unchanged. Treatments were carried out in quadruplicates (n=4) and reported as mean percentage drug permeated ±SD.

Effect of MKT NPs on Tau Level in a Cellular AD Model

Figure 5A:
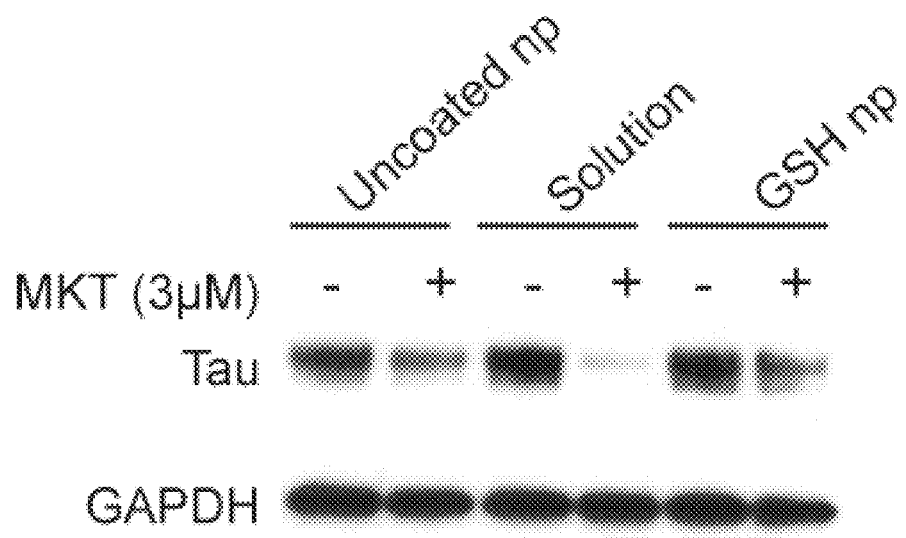
FIG. 5A illustrates MKT nanoparticles decreasing tau levels in a cellular model. HeLa cells stably transfected with human tau were treated for 24 hours with uncoated/Unc np (Vehicle − or MKT+) or solution (Vehicle − or MKT+) or GSH np (Vehicle − or MKT +).
Figure 5B:
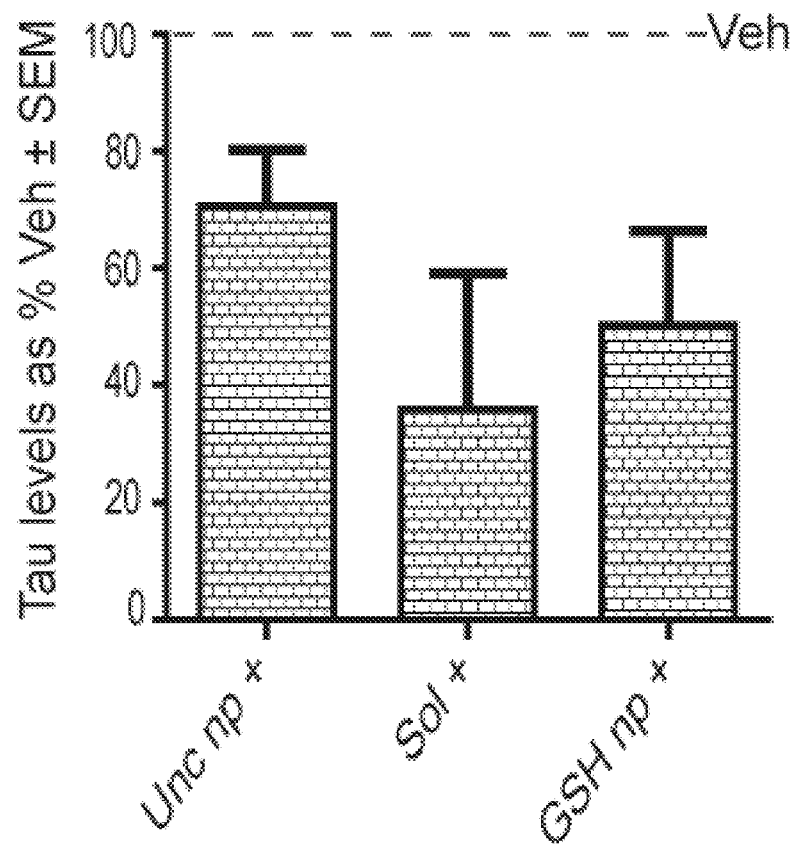
FIG. 5B is a quantification plot of the Western blot (see FIG. 5A) after GAPDH normalization and comparison with respective vehicle (veh) control show reduction in tau level by MKT. Replicate blots were used for the analysis. 73×115 mm (150×150 DPI)

In order to determine whether the newly formulated MKT-NPs are active, a cellular AD HeLa cell model that stably expresses human tau was used. Cells were treated with 3 µM of MKT uncoated NPs or MKT Glu-NPS or drug in solution or various controls for 24 hours. Western blot analysis of samples showed that treatment with MKT Glu-NPs causes a similar reduction in tau levels as MKT in solution (FIGS. 5A-5B), though as discussed MKT in solution cannot permeate the BBB effectively, as MKT Glu-NPs can. Further, uncoated MKT NPs showed slightly lower reduction in tau compared to MKT in solution (FIGS. 5A-5B). Overall, cellular data suggests MKT Glu-NPs are functionally active and effective to reducing tau levels.

DISCUSSION

The NPs were formulated according to the nanoprecipitation method, which employs the use of two distinct phases of formulation: oil phase and water phase. The oil phase is comprised of the NP vector and drug, and the water phase is that from which the oil phase solvent evaporates to cause the precipitation of the NP formulations. NPs developed by this method exhibit spherical structures and maintain physical integrity and proper morphology suitable for intravitreal injection and drug delivery. Coating of GSH onto the NPs does not compromise the physical integrity of the NPs formulations. The GSH exists on the outer layer of the NP formulation and is thought to coat the NP polymer through electrostatic interactions between the side chains of the GSH molecule and charged functional groups of the PEG component of the PEG-PLGA vector [14].

FIG. 1 depicts a representation of the MKT Glu-NP formulations. The drug MKT is encapsulated in the hollow sphere created by the self-assembly of hydrophobic NP vector lipid chains in water phase upon the evaporation of the oil phase solvent.

The sizes of the NPs formulations were over 200 nm. The sizes of the MKT NPs were significantly greater than that of the blank NPs, which suggests that the increase in MKT NPs size can be attributed to the presence of drug molecule in the NPs. Furthermore, the smaller size of the MKT Glu-NPs as compared to the MKT NPs may be attributed to the GSH coating of the NPs, which may induce a more compact shape due to the very hydrophilic nature of GSH [20]. In addition, the lower sizes of the MKT Glu-NPs may also be attributed to displacement of any MKT existing on the surface of the NPs by GSH [18]. The sizes of NPs in each formulation were normally distributed as suggested by PDI data.

Contrarily, monodisperse formulations have greater particle size fluctuations which may induce excessive aggregation in solution [18]. SEM data confirmed the uniform size distribution of the NPs formulations, as the SEM micrographs of NPs showed spherical morphology with fine particles. The GSH coating of the MKT Glu-NPs can be confirmed by the reflective coat of the formulations as observed in the SEM data. The size data obtained from the MKT Glu-NP formulations suggest that the formulation is suitable for intravenous delivery and BBB permeation [25].

An issue present in the formulation of NPs encapsulating hydrophilic drugs is their rapid escape into the water phase without proper encapsulation by the NPs [26]. The cause of this complication is the lowered encapsulation efficiency as compared to that of hydrophobic drugs. However, the encapsulation efficiency of nearly 30% seen in the present study is adequate for any future in vivo experimentation due to appropriate and physiologically relevant amount of MKT present in the NPs formulations. Any alteration in the NP formulation method through changes in amounts of drug and polymer chosen would likely lower the encapsulation efficiency of derived NP formulations.

The NP formulations exhibited sustained release of MKT from the polymer. MKT NP and MKT Glu-NP formulations had an initial burst release profile, which is the release of unencapsulated drug that exists on the surface of the NPs. The drug solution exhibited a rapid release of the drug in the initial 4 hours of investigation that remained consistent over the remainder of the study. The MKT Glu-NPs exhibited sustained release of the drug over 72 hours until complete release was achieved. MKT NPs were able to release approximately 20% of the drug by the end of the study. The delayed release of the MKT NPs could be due to the slower degradation of the polymer matrix of PEG-PLGA. Drug release from NP polymers occurs mainly through diffusion and swelling-induced lysing of the NP matrix. In addition, the long chains of the PEG-PLGA polymer induce the attraction of water molecules to the NP matrix to enter the NPs and release drug through hydration [27]. It is assumed that the rapid release of drug from the MKT Glu-NPs could be induced by greater attraction of water by the hydrophilic GSH-coated surface of the MKT Glu-NPs which would lead to greater hydration and release of drug from the NPs matrix. It is reasonable to assume that drug release profiles of MKT from MKT Glu-NP formulations may differ in in vivo situations due to the complex interactions of the NPs with biological compounds.

Proper BBB physiology is maintained by the adequate expression of tight junctions in brain endothelial cells through interactions with associated neuroglial cells to block the permeation of potentially toxic substances into neural tissue [28]. TEER values measure the endothelial resistance of the TRANSWELL model which, in turn, determines whether the appropriate tight junctional barrier is maintained by the BBB model for the proper replication of physiological phenomenon [23]. TEER values obtained from the TRANSWELL model in the current study ranged from about 231.84 $\Omega cm^2$ to about 313.6 $\Omega cm^2$ prior to treatment with drug solution and NP formulations and from about 271.04 $\Omega cm^2$ to about 356.16 $\Omega cm^2$ following treatment. The TEER values were significantly increased at the end of the 48-hour study period suggesting the increased expression of tight junctions in endothelial cells throughout the study period. The reported TEER values in the present study are higher than those previously reported for mono-, co-, and tri-cultures of human microvascular endothelial cells with human astrocyte and pericyte cells grown on TRANSWELL permeable inserts similar to the methodology described herein [23], suggesting that the TRANSWELL in vitro BBB model in the current study is a physiologically-relevant indicator of trans-BBB permeation of drug compounds.

Treatments with drug solution, MKT NPs, and MKT Glu-NPs in the TRANSWELL BBB model revealed that the MKT Glu-NPs permeate through the BBB at greater rates than both drug solution and MKT NPs. It is reasonable to believe that the greater rate of MKT Glu-NP permeation is due to the endocytosis of MKT Glu-NPs by the endothelial cells to allow passage through the BBB. In addition, it was surprising to find that the MKT Glu-NPs showed a drastic increase in BBB permeation between 24-48 hours of the study period despite the increased expression of tight junctional proteins in endothelial cells of the TRANSWELL model, as evidenced by the significantly greater TEER values after the study was completed. In other words, despite the increased expression of tight junctional proteins, which would typically lead to less permeation through the BBB, MKT Glu-NPs were still capable of effectively permeating the BBB.

Functionality of newly generated MKT-NPs was tested in a well-characterized cellular model of AD and tauopathies as described previously [18]. As seen in FIGS. 5A-5B, treatment with MKT Glu-NPs and MKT-solution showed greater and comparable reduction in tau levels. However, the uncoated MKT-NP formulation showed slightly lower reduction in tau level (FIGS. 5A-5B), which can be explained by the fact that MKT NPs had lower permeation than both the drug solution and MKT Glu-NPs, due to the blockage of lipid-compound permeation through the BBB. The current inventors have previously reported the trans-BBB permeation of a number of GSH-coated NP formulations [14, 18, 20, 21] and have reported the permeation of GSH-coated NPs in C57BL/6 mouse model when injected peritoneally [20]. Similar BBB permeation results can be expected in animal models of AD when injected with MKT Glu-NPs of MKT.

CONCLUSION

The present study formulated and characterized NPs encapsulating MKT and enabled the brain targeting of the NPs formulations. The NPs were successfully formulated with biologically compatible vector and particle size as well as uniform size distribution. GSH was successfully coated onto the surface of the NPs, and induced greater and more sustained drug release profile in solution as compared to drug solution and MKT NPs. The MKT Glu-NPs were shown to permeate a physiologically-relevant in vitro model of the BBB better than the drug solution and MKT NPs. MKT Glu-NPs showed functional and similar reduction in tau levels, like MKT in solution, in a cellular model of AD and tauopathies. Taken together, the data enables targeting of the brain with the described MKT Glu-NP formulation for the reduction of tau-related pathology in models of AD.

It is further expected that the MKT Glu-NP formulation would be effective in providing anti-cancer effects in a subject or patient, based on [32], of which a current co-inventor is a co-author, where MKT was seen to have anti-cancer effects.

REFERENCES

1. Kolarova, M., et al., Structure and pathology of tau protein in Alzheimer disease. International journal of Alzheimer's disease, 2012. 2012.
2. Jeganathan, S., et al., The Natively Unfolded Character of Tau and Its Aggregation to Alzheimer-like Paired Helical Filaments†. Biochemistry, 2008. 47(40): p. 10526-10539.
3. Friedhoff, P., et al., Structure of tau protein and assembly into paired helical filaments. Biochimica et Biophysica Acta (BBA)-Molecular Basis of Disease, 2000. 1502(1): p. 122-132.
4. Hyman, B. T., J. C. Augustinack, and M. Ingelsson, Transcriptional and conformational changes of the tau molecule in Alzheimer's disease. Biochimica et Biophysica Acta (BBA)-Molecular Basis of Disease, 2005. 1739(2): p. 150-157.
5. Garcia-Sierra, F., et al., Conformational changes and truncation of tau protein during tangle evolution in Alzheimer's disease. Journal of Alzheimer's Disease, 2003. 5(2): p. 65-77.
6. Maccioni, R. B., J. P. Munoz, and L. Barbeito, The molecular bases of Alzheimer's disease and other neurodegenerative disorders. Archives of medical research, 2001. 32(5): p. 367-381.
7. Thies, W. and L. Bleiler, 2013 Alzheimer's disease facts and figures. Alzheimer's & dementia: the journal of the Alzheimer's Association, 2013. 9(2): p. 208-245.
8. Miyata, Y., et al., Synthesis and initial evaluation of YM-08, a blood-brain barrier permeable derivative of the heat shock protein 70 (Hsp70) inhibitor MKT, which reduces tau levels. ACS chemical neuroscience, 2013. 4(6): p. 930-939.
9. Propper, D., et al., Phase I trial of the selective mitochondrial toxin MKT 077 in chemoresistant solid tumours. Annals of oncology, 1999. 10(8): p. 923-927.
10. Koren III, J., et al., Rhodacyanine derivative selectively targets cancer cells and overcomes tamoxifen resistance. PloS one, 2012. 7(4): p. e35566.
11. Jinwal, U. K., et al., Hsc70 rapidly engages tau after microtubule destabilization. Journal of biological chemistry, 2010. 285(22): p. 16798-16805.
12. Weisberg, E. L., et al., In vivo administration of MKT causes partial yet reversible impairment of mitochondrial function. Cancer research, 1996. 56(3): p. 551-555.
13. Tatsuta, N., et al., Pharmacokinetic analysis and antitumor efficacy of MKT, a novel antitumor agent. Cancer chemotherapy and pharmacology, 1999. 43(4): p. 295-301.
14. Grover, A. H., Anjali; Pathak, Yashwant; Sutariya, Vijaykumar, Brain-Targeted Delivery of Docetaxel by Glutathione-Coated Nanoparticles for Brain Cancer. AAPS PharmSciTech, [In Press. Accepted 28th May, 2014].
15. Danhier, F., et al., PLGA-based nanoparticles: an overview of biomedical applications. Journal of controlled release, 2012. 161(2): p. 505-522.
16. Wacker, M., Nanocarriers for intravenous injection—The long hard road to the market. International journal of pharmaceutics, 2013. 457(1): p. 50-62.
17. Valdovinos-Flores, C. and M. E. Gonsebatt, The role of amino acid transporters in GSH synthesis in the blood-brain barrier and central nervous system. Neurochemistry international, 2012. 61(3): p. 405-414.
18. Jinwal, U. K., et al., Preparation and Characterization of Methylene blue Nanoparticles for Alzheimer's disease and other Tauopathies. Curr Drug Deliv, 2013.
19. Carroll, R. T., et al., Brain-targeted delivery of Tempol-loaded nanoparticles for neurological disorders. Journal of drug targeting, 2010. 18(9): p. 665-674.
20. Geldenhuys, W., et al., Brain-targeted delivery of paclitaxel using glutathione-coated nanoparticles for brain cancers. Journal of drug targeting, 2011. 19(9): p. 837-845.
21. Geldenhuys, W., et al., Brain-targeted delivery of doxorubicin using glutathione-coated nanoparticles for brain cancers. Pharmaceutical development and technology, 2014(0): p. 1-10.
22. Lee D H, Rotger C, Appeldoorn C C, et al. Glutathione PEGylated liposomal methylprednisolone (2B3-201) attenuates CNS inflammation and degeneration in murine myelin oligodendrocyte glycoprotein induced experimental autoimmune encephalomyelitis. J Neuroimmunol 2014; 274(1-2): 96-101.
23. Hatherell, K., et al., Development of a three-dimensional, all-human *in vitro* model of the blood-brain barrier using mono-, co-, and tri-cultivation TRANSWELL models. Journal of neuroscience methods, 2011. 199(2): p. 223-229.
24. Garcia, C. M., et al., Endothelial cell-astrocyte interactions and TGFβ are required for induction of blood-neural barrier properties. Developmental brain research, 2004. 152(1): p. 25-38.
25. Hatakeyama, H., et al., Factors governing the in vivo tissue uptake of transferrin-coupled polyethylene glycol liposomes in vivo. International journal of pharmaceutics, 2004. 281(1): p. 25-33.
26. Bilati, U., E. Allémann, and E. Doelker, Development of a nanoprecipitation method intended for the entrapment of hydrophilic drugs into nanoparticles. European Journal of Pharmaceutical Sciences, 2005. 24(1): p. 67-75.
27. Wischke, C. and S. P. Schwendeman, Principles of encapsulating hydrophobic drugs in PLA/PLGA microparticles. International Journal of pharmaceutics, 2008. 364(2): p. 298-327.
28. Cecchelli, R., et al., Modelling of the blood-brain barrier in drug discovery and development. Nature Reviews Drug Discovery, 2007. 6(8): p. 650-661.
29. Ghaffarian, R., Muro, S. Models and Methods to Evaluate Transport of Drug Delivery Systems Across Cellular Barriers. *J. Vis. Exp.* (80), e50638, doi:10.3791/50638 (2013).
30. Etame, A. B., Smith, C. A., Chan, W. C. W., Rutka, J. T. Design and Potential Application of PEGylated Gold Nanoparticles with Size-Dependent Permeation Through Brain Microvasculature, Nanomedicine: Nanotechnology, Biology, and Medicine, 2011, 7, 992-1000.
31. Garberg, P., Ball, M., Borg, N., Cecchelli, R., Fenart, L., Hurst R. D., Lindmark, T., Mabondzo, A., Nilsson, J. E., Raub, T. J., Stanimirovic, D., Terasaki, T., Oberg, J. O., Osterberg, T. In Vitro Models for the Blood-Brain Barrier. Toxicol in Vitro, 2005, 19, 299-334.
32. Koren J III et al. (2012) Rhodacyanine Derivative Selectively Targets Cancer Cells and Overcomes Tamoxifen Resistance. PLoS ONE 7(4): e35566. doi:10.1371/journal.pone.0035566.
33. Paul R. Lockmana et al., Brain uptake of thiamine-coated nanoparticles, Journal of Controlled Release 93 (2003) 271-282.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating a cancer in a subject, comprising administering a therapeutically effective amount of a composition comprising a nanoparticle comprising MKT-077 encapsulated by a biocompatible, non-toxic polymer coated by glutathione and a plurality of poly(ethylene glycol) end groups around a surface of each nanoparticle, to the subject, wherein about 100% of said MKT-077 has a sustained release from said nanoparticles over about 72 hours, and wherein MKT-077 crosses a blood-brain barrier of the subject, and wherein the cancer is selected from the group consisting of melanoma and carcinoma of colon, breast and pancreas.

2. The method of claim 1, wherein said biocompatible, non-toxic polymer includes poly(ethylene glycol)ylated poly-(lactide-co-glycolide) to encapsulate said MKT-077.

3. The method of claim 1, wherein said biocompatible, non-toxic polymer is hydrophilic to facilitate an interaction of said glutathione with transporters present on said blood-brain barrier.

4. The method of claim 1, wherein said nanoparticles are coated in 2% w/v of said glutathione.

5. The method of claim 1, wherein said nanoparticles have a size of less than about 300 nm.

6. The method of claim 1, wherein said plurality of poly(ethylene glycol) end groups extend further away from said surface of said each nanoparticle than said glutathione disposed on said surface of said each nanoparticle in order to provide a surface area of said plurality of poly(ethylene glycol) end groups to interact with transporters present on said blood-brain barrier.

* * * * *